United States Patent [19]

Boyd

[11] Plant 4,627

[45] Jan. 20, 1981

[54] DOGWOOD TREE-PURPLE GLORY VARIETY

[75] Inventor: Clark C. Boyd, McMinnville, Tenn.

[73] Assignee: The Boyd Brothers Company, McMinnville, Tenn.

[21] Appl. No.: 17,170

[22] Filed: Mar. 2, 1979

[51] Int. Cl.[3] ..... A01H 5/00

[52] U.S. Cl. ..... Plt./51

[58] Field of Search ..... Plt./51

*Primary Examiner*—Robert E. Bagwill

*Attorney, Agent, or Firm*—Burns, Doane, Swecker & Mathis

[57] ABSTRACT

A new and distinct variety of Pink Flowering Dogwood, botanically known as *Cornus florida* is provided. The new variety exhibits a rapid upright growth habit and most nearly resembles the Sweetwater Red Flowering Dogwood (non-patented), but primarily is distinguished therefrom by the distinctive coloration of the foliage (as illustrated). The foliage initially is light purple and changes to dark purple as the leaves mature. Such foliage coloration substantially is retained throughout the growing season and into the fall even when grown in full sunlight.

1 Drawing Figure

SUMMARY OF THE INVENTION

The new and distinct variety of Pink Flowering Dogwood tree was discovered in 1966 while growing within a block of approximately 250,000 *Cornus florida* seedlings on the cultivated nursery property of the assignee located near McMinnville, Tenn. The seed which yielded the new variety was planted in 1965 and likely was obtained from either the Pink Flowering Dogwood variety or the Sweetwater Red Flowering Dogwood variety. Accordingly, the new variety is believed to be a chance seedling or mutation of unknown parentage which differs from all prior known dogwood varieties of which I am aware.

At the time of my discovery my attention was attracted to a single plant in the seedling block which was significantly different in appearance from all other plants in the block because of its unusual purple leaf coloration. Steps were taken by me carefully to preserve and to continue to observe this unusual seedling. Asexual reproduction by buddings at the nursery of the assignee beginning in 1968 confirmed that the distinctive appearance of the new variety comes true and is established and transmitted through succeeding propagations.

The new and distinct variety of dogwood tree has been named the Purple Glory variety.

BRIEF DESCRIPTION OF THE PHOTOGRAPH

The accompanying photograph shows a typical specimen of the new variety grown at McMinnville, Tenn., as depicted in color as nearly true as it is reasonably possible to make the same in a color illustration of this character. On the left is the distinctive purple foliage of the new dogwood variety of the present invention, and on the right for comparative purposes is foliage of the Pink Flowering Dogwood variety (*Cornus florida rubra*). The photograph was obtained on about August 1.

DETAILED DESCRIPTION OF NEW VARIETY

The following description was made from plants growing at McMinnville, Tenn. Color terminology is to be accorded its ordinary dictionary significance. Unless otherwise stated the new variety has characteristics substantially identical to those of the Sweetwater Red Flowering Dogwood variety (non-patented).

Growth habit: Rapid, upright.

Foliage: The leaves initially are light purple on both upper and lower surfaces. As the leaves mature, this light purple coloration gradually changes to a dark purple coloration (as illustrated). Additionally, some mature leaves partially may exhibit a suffused dark green appearance (as illustrated) in addition to the dark purple coloration. The distinctive purple coloration is substantially retained throughout the growing season and into the fall when frost removes the foliage. The purple coloration is neither lost nor diminished even when the tree is grown in unobstructed sunlight. The leaf coloration of the present variety readily can be distinguished from that of the Sweetwater Red Flowering Dogwood variety (non-patented) and the Cherokee Chief Red Flowering Dogwood variety (U.S. Plant Pat. No. 1,710) in that the leaves of both of these varieties assume a substantially uniform dark green coloration during the summer months. With reference to the R.H.S. Colour Chart of the Royal Horticultural Society the mature leaf coloration of the present variety commonly approaches that of the Greyed-Purple Group 183B suffused with dark green.

*Blossoms.*—The blossoms consist of four dark red bracts and are approximately 3 to 4 inches in diameter. When grown at McMinnville, Tenn., blossoms commonly are present during the last week of April throughout most of May.

Seeds: The seeds formed are slightly smaller than those of the Sweetwater Red Flowering Dogwood variety.

Silvical character: Good disease resistance is exhibited by the present variety. Also, trees of the variety repeatedly have withstood winter temperatures of −15° F. without deleterious results.

I claim:

1. A new and distinct variety of Pink Flowering Dogwood tree, botanically known as *Cornus florida,* substantially as illustrated and described, characterized particularly as to novelty by the unique combination of (1) a rapid upright growth habit, (2) distinctive leaf coloration which initially is light purple changing to dark purple as the leaves mature, and (3) the ability substantially to retain said purple leaf coloration throughout the growing season and into the fall even when the tree is grown in full sunlight.

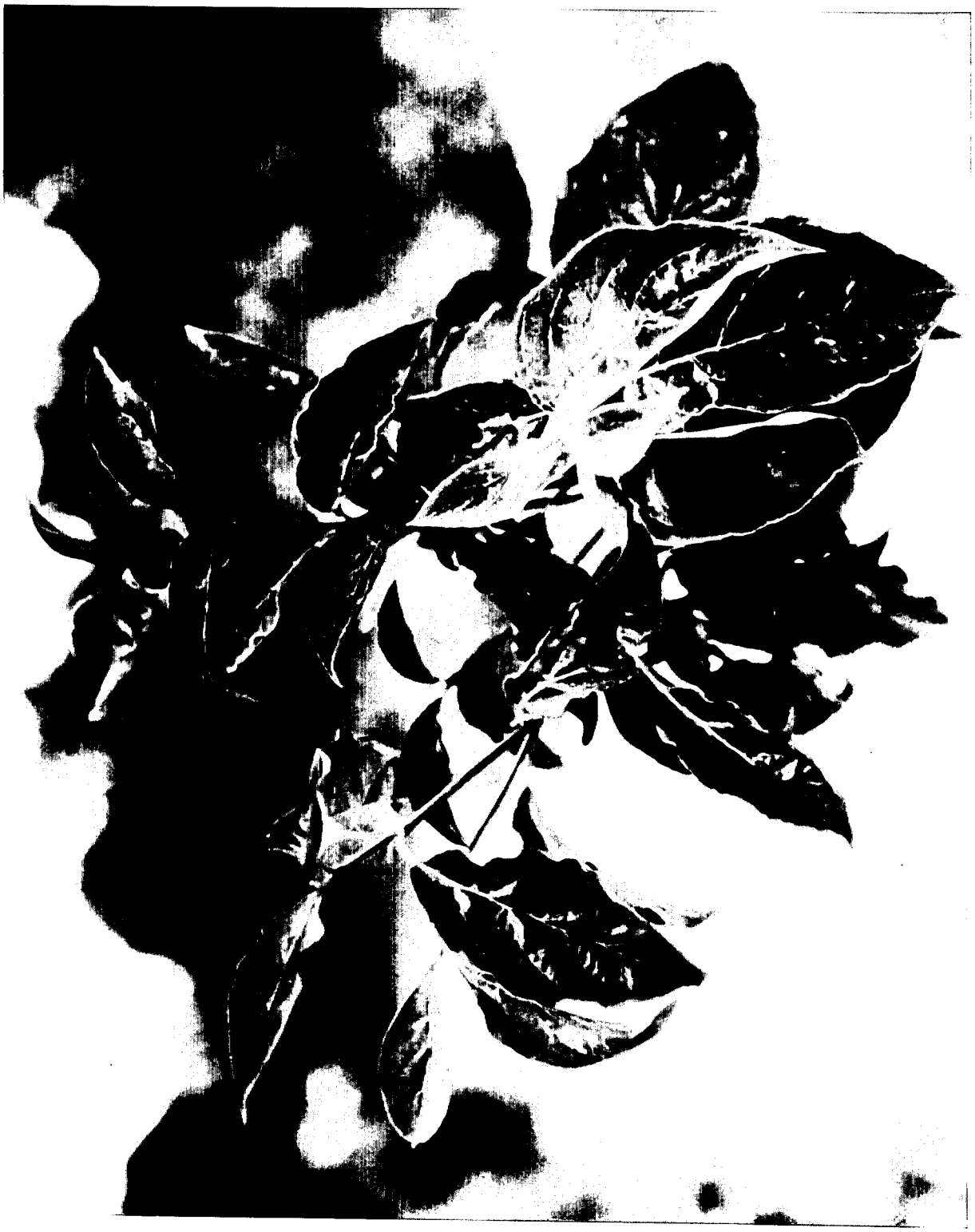

* * * * *